United States Patent [19]

Pakebusch et al.

[11] 4,439,527

[45] Mar. 27, 1984

[54] COMPOSITION AND METHOD FOR THE DETECTION OF HYDROGEN PEROXIDE

[75] Inventors: Bernd Pakebusch, Hessheim; Carsten A. Carstensen, Heuchelheim; Bernward Sojka, Viernheim; Hans Lange, Lampertheim, all of Fed. Rep. of Germany

[73] Assignee: Boehringer Mannheim GmbH, Mannheim, Fed. Rep. of Germany

[21] Appl. No.: 385,760

[22] Filed: Jun. 7, 1982

[30] Foreign Application Priority Data

Jun. 30, 1981 [DE] Fed. Rep. of Germany ....... 3125667

[51] Int. Cl.³ .................... G01N 21/78; G01N 33/50
[52] U.S. Cl. ...................... 436/135; 422/56; 422/61; 435/28; 436/904; 548/358
[58] Field of Search ............... 436/66, 95, 135, 904; 422/56, 57, 61; 435/14, 28; 548/358

[56] References Cited

U.S. PATENT DOCUMENTS

| Re. 29,498 | 12/1977 | Meiattini | 435/28 X |
|---|---|---|---|
| 4,078,892 | 3/1978 | Steinbrink, Jr. | 422/61 X |
| 4,098,574 | 4/1978 | Dappen | 435/28 X |
| 4,247,631 | 1/1981 | Nix et al. | 436/164 X |
| 4,251,629 | 2/1981 | Yamanisi et al. | 435/28 |

FOREIGN PATENT DOCUMENTS 24578  3/1981  European Pat. Off. .

OTHER PUBLICATIONS

Grillo et al., "Clinical Chemistry", 27/3, 375-379 (1981).

Primary Examiner—Arnold Turk
Attorney, Agent, or Firm—Felfe & Lynch

[57] ABSTRACT

Means and method for the detection of hydrogen peroxide or of hydrogen peroxide-forming substrates, consisting of 4-aminoantipyrine and an aromatic amine or phenol and a neutral to weakly acid buffer as well as other additives and reagents which form $H_2O_2$ with the substrate and which are known for use in Trinder's reaction, the 4-aminoantipyrine, in the immiscible state before use, being separate from the acid buffer and from the other reagents if any, and being mixed with a small amount of an alkaline buffer having a pH of 8.5 to 14.0, the two compositions being combined, in a quantity ratio to one another that is suitable for the detection test, in a single package or in a single-use unit.

6 Claims, No Drawings

COMPOSITION AND METHOD FOR THE DETECTION OF HYDROGEN PEROXIDE

This invention relates to a composition and a method for the detection of hydrogen peroxide. More specifically, the invention relates to such a composition and method utilizing oxidative condensation of chromogens in the presence of peroxidase.

The analytic determination of hydrogen peroxide is very important in medical diagnosis, because in a greater number of important test methods, hydrogen peroxide is formed as an intermediate, which then is transformed to an optically measurable substance by reaction with suitable chromogenic substances, mostly in the presence of a peroxidase (POD) as catalyst. The degree to which the optically measurable product forms serves as a measure of the amount of the hydrogen peroxide or as a measure of the substrate forming the hydrogen peroxide. Examples of such reactions are the detection of glucose with glucose oxidase, cholesterol with cholesterol oxidase and uric acid with uricase. Numerous chromogens and indicator systems have been proposed for this reaction. One of the most frequently used indicator systems is Trinder's (Biochem. 6 (1969) 24–27), in which phenol is oxidatively coupled with 4-aminoantipyrine (4-AAP) in the presence of POD under the action of $H_2O_2$. Instead of phenol, phenol derivatives, aniline derivatives, naphthene, naphthene derivatives or similarly reacting substances can also be used. Instead of 4-aminoantipyrine, other aminoantipyrine derivatives, vanillin diaminesulfonic acid, methylbenzothiazolone hydrazone (MBTH), sulfonated methylbenzothiazolone hydrazone (SMBTH) and similarly reacting compounds can be used.

Although 4-AAP is known as a sensitive reagent in this reaction, it nevertheless has certain disadvantages. In particular, in the case of the commercially available reagents, it is found that, if the concentration of the dye that is formed is plotted against the concentration of the oxidizing agent ($H_2O_2$ or a substrate forming $H_2O_2$), there is a linear relationship over wide ranges of concentration, but at low concentrations negative dye concentrations are extrapolated. This is to be attributed to the fact that even highly purified 4-AAP in the test mixture, under the stress of relatively long storage, forms to a slight extent degradation products of unknown constitution, which reduce $H_2O_2$ and thus withdraw it from the actual test reaction.

The problem has therefore been created of stabilizing 4-AAP such that no amounts or only negligible amounts of the above degradation products will form in the test systems even in the case of relatively long storage.

THE INVENTION

Surprisingly it has been found that this problem can be solved by storing the 4-AAP in mixture with a small amount of an alkaline buffer in the pH range of 8.5 to 14.0, and, just before the test reaction, adding a larger amount of buffer of a pH of 5.0 to 8.0 to bring it into the range required for the enzymatic reaction to proceed.

The two compositions are combined in a single package or in a single-use unit in a ratio to one another that is appropriate for the test. The term single package means that the preparations packed in two different containers, usually in an amount intended for several tests, are contained in a common enveloping package. The term single-use unit means that the preparations are in a common package, but are physically separated from one another and are not combined until the test fluid is added. Examples that can be mentioned are separation in two tablets, multiple-layer tablets, multiple-layer lyophilizates, contained, if desired, in a cell serving as a reaction vessel. It is especially preferred to impregnate absorbent carriers with each of the two compositions and to fasten two pieces of each to a handle so that, when they are dipped in the test fluid the desired amounts of the two components are dispensed simultaneously.

Since aromatic amines are normally relatively stable in a neutral or acid medium, but are subject to oxidative decomposition in an alkaline medium, it appears to be extraordinarily surprising that 4-AAP can be stabilized precisely in the latter range.

Any alkaline buffer can be used for this purpose which establishes the desired pH range and is compatible with the other reagents, especially the enzymes used. Examples are alkali carbonate/bicarbonate buffers, borate buffers, phosphate buffers, glycine buffers, veronal buffers, and tris and tra buffers.

Examples of neutral or acid buffers in which the test reaction is performed are phosphate, citrate and acetate buffers.

Since the enzymes and other auxiliary reagents, and also the peroxidase required for the formation of $H_2O_2$ from the substrate in the above-mentioned tests are normally more stable in an acid medium than in an alkaline medium, it is advantageous to separate them from the 4-AAP and store them together with the "acid" buffer. The prepared reagent system is then prepared by mixing the two components together in the appropriate ratio shortly before performing the reaction. The two components are ordinarily stored in solid form as lyophilizates, powders or tablets, or used to impregnate absorbent carriers from which the reagent is prepared by the addition of water, or which can also be added directly to the dissolved sample.

A number of applications of the invention are described in the following examples.

EXAMPLE 1

Dye Test for Glucose with a Mixture of 4-Aminoantipyrine, GOD and POD

A reagent strip 10 mm wide and about 98 mm long, to the bottom end of which two patches of a 10×15 mm surface are fastened apart from one another, one of which contains 7.7 mg of 4-aminoantipyrine together with 757 micrograms of $NaHCO_3$ and 878 micrograms of $Na_2CO_3$, impregnated in filter paper (598 Schleicher & Schüll) from an aqueous solution (pH=10.5), and the other contains 900 units of glucose oxidase and 55 units of peroxidase impregnated into a polyamidecellulose mat (Binzer VS 532) from 0.1 molar phosphate buffer pH=6.0, is eluted in 50 ml of an 0.1 molar phosphate buffer solution pH=7.0 containing 10 millimoles of phenol per liter. 0.1 ml of serum dealbuminated with uranyl acetate is pipetted into 2 ml of this solution and thoroughly mixed, and the reaction mixture is let stand for 30 minutes at room temperature.

The color reaction completed after this time is measured at 505 or 546 nanometers. The linearity test of 0–600 mg of glucose per liter with reagent strips stored for 6 and 12 weeks at 35° C. with the exclusion of light and moisture, eluted in fresh 0.1 molar phosphate buffer solution of pH=7.0 with mmol/l of phenol shows that a virtually negligible negative axial intercept occurs.

| Reagent Strip | Regression |
|---|---|
| fresh | y = 0.00230 × +0.0019 |
| 6 weeks at 35° C. | y = 0.00231 × −0.0022 |
| 12 weeks at 35° C. | y = 0.00230 × −0.0040 |

If reagent strips prepared in a similar manner, in which the 4-aminoantipyrine paper is buffered to pH=7.0 with phosphate buffer, are compared, then, as the exposure time increases, an increasing negative axial intercept results.

| Reagent strip | Regression |
|---|---|
| Fresh | y = 0.00227 × +0.0026 |
| 6 weeks at 35° C. | y = 0.00220 × −0.013 |
| 12 weeks at 35° C. | y = 0.00230 × −0.029 |

EXAMPLE 2

Cholesterol Color Test with 4-Aminoantipyrine (CHE, CHO, POD)

A reagent strip 6 mm wide and about 75 mm long, to the bottom end of which two patches measuring 6×6 mm are fastened apart from one another, one of which contains 410 micrograms of 4-aminoantipyrine together with 84 micrograms of $NaHCO_3$ and 106 micrograms of $Na_2CO_3$ impregnated into filter paper (Schleicher & Schüll 598 F) from aqueous solution (pH=10.0), and the other contains 0.3 units of cholesterinoxidase, 0.6 units of chlolesterinesterase, and 4.7 units of peroxidase impregnated into 598 F paper from 0.1 molar phosphate buffer solution pH 7.5 containing 10 mmol/l of phenol, is eluted.

To this solution, 0.02 ml of serum is added with a pipette and thoroughly mixed, and the reaction mixture is let stand for 30 minutes at room temperature. The color reaction completed after this period is measured at 505 or 546 nm. The linearity testing 0–400 mg of cholesterol per dl with reagent strips stored for 6 and 12 weeks at 35° C. with the exclusion of light and moisture, eluted in fresh phosphate buffer solution pH=7.5 containing 10 mmol/l of phenol, shows that no negative axial intercept takes place.

| Reagent strip | Regression |
|---|---|
| fresh | y = 0.0012 × +0.0003 |
| 12 weeks at 35° C. | y = 0.0012 × −0.003 |

If reagent strips prepared in a similar manner, in which the 4-aminoantipyrine paper is buffered to pH 7.0 with phosphate buffer, an increasing negative axial intercept results as the storage time increases.

| Reagent strip | Regression |
|---|---|
| fresh | y = 0.0012 × +0.0007 |
| 12 weeks at 35° C. | y = 0.0012 × −0.0160 |

EXAMPLE 3

Stabilization of 4-aminoantipyrine with various 0.1 molar buffers of pH=10.0

Linearity testing of 0–600 mg of glucose/dl at 546 nm

| Buffer Reagent strip | 0.1M $NaHCO_3/Na_2CO_3$ | 0.1M Piperazine Regression | 0.1M Glycine |
|---|---|---|---|
| Fresh | y = 0.00230 × +0.0019 | y = 0.00227 × −0.0032 | y = 0.00220 × −0.0022 |
| 6 wks. at 35° C. | y = 0.00231 × −0.0022 | y = 0.00227 × −0.0031 | y = 0.00226 × −0.0038 |
| Buffer Reagent strip | 0.1M Tris | 0.1M Triethanolamine Regression | 0.1M Veronal |
| Fresh | y = 0.00226 × −0.0010 | y = 0.00215 × −0.0004 | y = 0.00219 × −0.0040 |
| 6 wks. at 35° C. | y = 0.00226 × +0.0044 | y = 0.00225 × −0.0044 | y = 0.00223 × −0.0034 |

It will be understood that the specification and examples are illustrative but not limitative of the present invention and that other embodiments within the spirit and scope of the invention will suggest themselves to those skilled in the art.

What is claimed is:

1. Test kit for the detection of hydrogen peroxide or a hydrogen peroxide forming substrate comprising
   (i) an aromatic amine or phenol and a first buffer which is a neutral to weakly acidic; and
   (ii) 4-aminoantipyrine, in the immiscible state, separate from said first buffer and mixed with a small amount of a second buffer having a pH of 8.5 to 14.0, the ingredients (i) and (ii) being combined in a quantity ratio appropriate for the test.

2. Test kit as claimed in claim 1, also containing reagents to form hydrogen peroxide with hydrogen peroxide forming substrates.

3. Test kit as claimed in claim 1, wherein ingredient (i) contains additional reagents for the formation of $H_2O_2$ from a hydrogen peroxide formng substrate.

4. Test kit as claimed in claim 1, wherein both ingredients (i) and (ii) contain additional reagents for the formation of $H_2O_2$ from the hydrogen peroxide forming substrate.

5. Method of detecting hydrogen peroxide, which method comprises forming a detection composition by combining, shortly prior to use, a 4-aminoantipyrine stabilized with a small amount of a buffer having a pH of 8.5 to 14.0, with an excess of a buffer which is neutral to weakly acidic, and with reagents necessary for Trinder's reaction, contacting a sample with the combined detection composition and evaluation the resultant coloration as a measure of the hydrogen peroxide, or hydrogen peroxide forming substrate, present.

6. Method as claimed in claim 5 for determining a hydrogen peroxide forming substrate, wherein the combined detection composition also contains a reagent necessary to release hydrogen peroxide from a hydrogen peroxide forming substrate.

* * * * *